United States Patent
Ando et al.

(10) Patent No.: US 11,149,249 B2
(45) Date of Patent: Oct. 19, 2021

(54) BASE MATERIAL FOR CELL CULTURE AND CELL CULTURE METHOD USING SAME, CELL CULTURE CONTAINER, AND USE AS BASE MATERIAL

(71) Applicant: MITSUBISHI GAS CHEMICAL COMPANY, INC., Tokyo (JP)

(72) Inventors: Haruna Ando, Niigata (JP); Shin Iida, Tokyo (JP); Yasunori Yamaguchi, Hiroshima (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 77 days.

(21) Appl. No.: 15/760,000

(22) PCT Filed: Sep. 23, 2016

(86) PCT No.: PCT/JP2016/078126
§ 371 (c)(1),
(2) Date: Mar. 14, 2018

(87) PCT Pub. No.: WO2017/051913
PCT Pub. Date: Mar. 30, 2017

(65) Prior Publication Data
US 2018/0265838 A1 Sep. 20, 2018

(30) Foreign Application Priority Data
Sep. 25, 2015 (JP) .............................. JP2015-187846

(51) Int. Cl.
| | | |
|---|---|---|
| *C12N 5/00* | (2006.01) | |
| *C08L 67/02* | (2006.01) | |
| *C08G 63/672* | (2006.01) | |
| *C12M 1/00* | (2006.01) | |

(52) U.S. Cl.
CPC ......... *C12N 5/0068* (2013.01); *C08G 63/672* (2013.01); *C08L 67/02* (2013.01); *C12M 23/20* (2013.01); *C08L 2203/02* (2013.01); *C12N 2533/30* (2013.01)

(58) Field of Classification Search
None
See application file for complete search history.

(56) References Cited

U.S. PATENT DOCUMENTS

| | | | | | |
|---|---|---|---|---|---|
| 7,064,169 | B2 * | 6/2006 | Ikeda | ........................ | C08J 5/18 525/444 |
| 7,199,103 | B2 * | 4/2007 | Bhatnagar | ............... | A61L 27/34 514/16.7 |
| 2004/0029266 | A1 * | 2/2004 | Barbera-Guillem | ... | C12M 23/04 435/297.5 |
| 2008/0299601 | A1 * | 12/2008 | Fike | ...................... | C12N 5/0068 435/29 |
| 2009/0181158 | A1 * | 7/2009 | Ikeya | ...................... | C12M 23/20 427/2.13 |
| 2010/0255447 | A1 * | 10/2010 | Biris | .................... | C09D 189/00 433/201.1 |
| 2011/0009327 | A1 * | 1/2011 | Hill | ......................... | A61P 19/04 514/16.7 |
| 2011/0229962 | A1 | 9/2011 | Mizutani et al. | | |
| 2012/0269785 | A1 * | 10/2012 | Woods | ...................... | A61P 1/16 424/93.7 |
| 2015/0320840 | A1 * | 11/2015 | Bamdad | ................. | A61K 38/45 424/93.7 |

FOREIGN PATENT DOCUMENTS

| | | |
|---|---|---|
| EP | 1 321 491 | 6/2003 |
| JP | H05-276923 | 10/1993 |
| JP | 2003182014 A * | 7/2003 |
| JP | 2007-504823 | 3/2007 |
| JP | 2008-104411 | 5/2008 |
| JP | 2013-116130 | 6/2013 |
| JP | 2014-205773 | 10/2014 |
| WO | 2005/034625 | 4/2005 |
| WO | 2010/044417 | 4/2010 |

OTHER PUBLICATIONS

Falco et al. J. Surgical Res. (2008) 149: 76-83 (Year: 2008).*
Machine translation of JP-2003182014-A, published 2003, downloaded from the JPO on Oct. 14, 2019 (Year: 2003).*
Sassoli et al. PLoS One (2012) 7(7): e37512; pp. 1-13 (Year: 2012).*
Wuertz et al. Biochem. Biophys. Res. Comm. (2009) 379: 824-829 (Year: 2009).*
Sharpe et al. British J. Derm. (2009) 161: 671673 (Year: 2009).*
Yang et al. J. Biomed. Mat. Res. (2002) 62(3): 438-446 (Year: 2002).*
Yukio Nakamura, ed., "Jikken Igaku (Experimental Medicine in English), Suppl, Cell culture protocol to be selected by objective", Yodosha Co., Ltd. (published on Mar. 20, 2012), p. 191.
Falco Erin E. et al., Recent Developments in Cyclic Acetal Biomaterials for Tissue Engineering Applications, Pharmaceutical Research, 2008, vol. 25, No. 10, p.2348-2356, ISSN 0824-8741.
Japu Christina et al., Bio-based poly(hexamethylene terephthalate)copolyesters containing cyclic acetalized tartrate units, Polymer, 2013, vol. 54, p. 1573-1582, ISSN 0032-3861.

* cited by examiner

*Primary Examiner* — Susan M Hanley
(74) *Attorney, Agent, or Firm* — Greenblum & Bernstein, P.L.C.

(57) ABSTRACT

The present invention provides a base material for cell culture comprising a polyester resin comprising a dicarboxylic acid unit and a diol unit, wherein 1 to 80% by mol of the diol unit is a diol unit having a cyclic acetal structure.

6 Claims, 2 Drawing Sheets

BASE MATERIAL FOR CELL CULTURE AND CELL CULTURE METHOD USING SAME, CELL CULTURE CONTAINER, AND USE AS BASE MATERIAL

TECHNICAL FIELD

The present invention relates to a base material for cell culture and a cell culture method using the same, etc. More specifically, the present invention relates to a base material for cell culture that is preferably used for the growth or proliferation of cells for use in the fields of medical science, regenerative medicine, biochemistry, and the like, and a cell culture method using the same, etc.

BACKGROUND ART

Various types of cell culture techniques for animals such as mice, monkeys, and primates have been studied so far. Such cell culture techniques are basic techniques, particularly in the fields of medical science, regenerative medicine, biochemistry, and the like. The cell culture techniques are used for the development of pharmaceutical products, the elucidation of pathological mechanisms, etc., in the field of medical science or biochemistry. Also, the cell culture techniques are used for the culture or differentiation of embryonic stem cells (ES cells) or induced pluripotent stem cells (iPS cells), the culture of cells of the skin, organs, or functional tissues such as dentary bone, etc., in the field of regenerative medicine.

Such cell culture is usually performed using a culture solution serving as a nutrient component in a predetermined container.

Cells are broadly classified, according to their properties, into two types: floating cells, which are cultured in a suspended state in a culture solution; and adherent cells, which are cultured in a state adhering to a container. Most of animal cells are adherent cells having adhesion dependency that allows the cells to grow while adhering to a material. In general, these adherent cells cannot survive for a long period in an ex vivo suspended state. Thus, the culture of the adherent cells requires a base material as a material for the adhesion of the cells.

Such a base material for use in the culture of the adherent cells (base material for cell culture) is generally a dish, a multi-dish, a microplate, a flask, or the like. The base material for cell culture is required to have transparency for the observation of cells or the inside, in addition to mechanical strength necessary for maintaining the shape.

It is known in general, but also depending on the type of cells or medium components in culture, that when a resin is used without surface treatment as a resin for use in the base material for cell culture, the resin resists the adhesion of adherent cells. Particularly, polymethylpentene, polyethylene terephthalate, polyethylene, polypropylene, ABS resins, and the like are known to resist the adhesion of cells (see, for example, Patent Literature 1).

In this context, the resin for use in the base material for cell culture is generally polystyrene. However, even if polystyrene is used in the base material for cell culture, adherent cells are less likely to adhere to a non-surface-treated polystyrene molding, though depending on the type of cells or medium components in culture. Accordingly, a polystyrene molding whose surface is rendered hydrophilic by low-temperature plasma treatment, corona discharge treatment, or the like is commercially available. Instruments for these purposes are widely used in the culture of adherent cells.

Thus, the culture face of the polystyrene molding can be coated with an animal-derived extracellular matrix such as gelatin or collagen, an animal-derived adhesion factor such as fibronectin or laminin, or a polymer such as poly-L-lysine to thereby enhance the adhesion properties and proliferation properties of cells.

For example, the culture face of a polystyrene container coated with gelatin can be obtained by applying a gelatin solution to the culture face of a polystyrene container so as to completely cover the culture face, leaving the polystyrene container at room temperature for 1 hour or longer, and then discarding the gelatin solution (see, for example, Non Patent Literature 1). Gelatin coating or collagen coating is known to enhance the adhesion properties and proliferation properties of cells. Products of polystyrene containers coated with gelatin or collagen are commercially available.

It is also known that the adhesion properties of cells are enhanced by coating the culture face of a container with polylysine such as poly-L-lysine or poly-D-lysine. Such a container coated with polylysine is suitable, particularly, for the culture of nerve cells (see, for example, Patent Literature 2).

Meanwhile, examples of a support for the base material for cell culture include polystyrene supports as mentioned above as well as glass, polypropylene, polyester, and polymethyl methacrylate supports (see, for example, Patent Literatures 3, 4, and 5).

CITATION LIST

Patent Literature

Patent Literature 1: International Publication No. WO2010/044417
Patent Literature 2: National Publication of International Patent Application No. 2007-504823
Patent Literature 3: Japanese Patent Laid-Open No. 5-276923
Patent Literature 4: Japanese Patent Laid-Open No. 2013-116130
Patent Literature 5: Japanese Patent Laid-Open No. 2008-104411

Non Patent Literature

Non Patent Literature 1: Yukio Nakamura, ed., "Jikken Igaku (Experimental Medicine in English), Suppl, Cell culture protocol to be selected by objective", Yodosha Co., Ltd. (published on Mar. 20, 2012), p. 191

SUMMARY OF INVENTION

Technical Problem

However, a base material using a polystyrene support may exhibit the insufficient adhesion of cells onto the base material, insufficient proliferation thereof though the proliferation is found to some extent, or the poor morphology of cells during proliferation, depending on the type of cells. In general, this tendency is pronounced, particularly, in primary culture in which cells collected from an organism are cultured for the first time.

A base material using a support other than the polystyrene support requires coating treatment for cell adhesion for using it. In addition, the required coating treatment increases cost.

In addition, for example, gelatin for use in a base material for cell culture disclosed in Non Patent Literature 1 is produced, for example, with the bovine or swine skin as a raw material. However, due to recent problems such as bovine spongiform encephalopathy (BSE) or foot-and-mouth disease, animal-derived gelatin or collagen is difficult to use in consideration of medical science, regenerative medicine, or the like. Even in the field of biochemistry or the like, gelatin or collagen is increasingly difficult to use because, for discarding a used gelatin solution, collagen solution, or gelatin- or collagen-coated container, it is necessary to take into consideration measures against leakage into environments.

On the other hand, polylysine disclosed in Patent Literature 2 is produced by bacterial fermentation or chemical synthesis and is therefore free from animal-derived components. Thus, the polylysine is easy to use in medical science or regenerative medicine, while it is also easy to discard a used polylysine solution or polylysine-coated container. However, since the polylysine is unstable, the effects of the polylysine on a container coated therewith are lost in 2 weeks in preservation at room temperature and also in 1 month at 4° C. Furthermore, due to this instability, a culture instrument coated with polylysine cannot be sterilized. Thus, for the commercial sales of a culture instrument coated with polylysine in advance, the coating with polylysine must be performed in an aseptic environment while conservation management after the coating are also difficult. In addition, there are cost problems.

An object of the present invention is to provide a base material for cell culture that allows adherent cells to proliferate at an excellent level without coating treatment.

Solution to Problem

The present inventors have conducted diligent studies in light of the object, and consequently completed the present invention by finding that cells can proliferate at an excellent level by using a polyester resin comprising diol units having a cyclic acetal structure as a base material for cell culture.

Specifically, the present invention relates to:

[1]

A base material for cell culture, comprising a polyester resin comprising a dicarboxylic acid unit and a diol unit, wherein 1 to 80% by mol of the diol unit is a diol unit having a cyclic acetal structure.

[2]

The base material for cell culture according to [1], wherein the diol unit having the cyclic acetal structure comprises a diol unit derived from at least one diol selected from a diol represented by general formula (1):

(1)

wherein $R^1$ and $R^2$ each independently represent a hydrocarbon group selected from the group consisting of an aliphatic hydrocarbon group having 1 to 10 carbon atoms, an alicyclic hydrocarbon group having 3 to 10 carbon atoms, and an aromatic hydrocarbon group having 6 to 10 carbon atoms, and a diol represented by general formula (2):

(2)

wherein $R^1$ is as defined above, and $R^3$ represents a hydrocarbon group selected from the group consisting of an aliphatic hydrocarbon group having 1 to 10 carbon atoms, an alicyclic hydrocarbon group having 3 to 10 carbon atoms, and an aromatic hydrocarbon group having 6 to 10 carbon atoms.

[3]

The base material for cell culture according to [1] or [2], wherein the diol unit having the cyclic acetal structure comprises a diol unit derived from 3,9-bis(1,1-dimethyl-2-hydroxyethyl)-2,4,8,10-tetraoxaspiro[5.5]undecane, or a diol unit derived from 5-methylol-5-ethyl-2-(1,1-dimethyl-2-hydroxyethyl)-1,3-dioxane.

[4]

The base material for cell culture according to any of [1] to [3], wherein the diol unit further comprises an additional diol unit other than the diol units having the cyclic acetal structure, wherein the additional diol unit comprises a diol unit derived from one or more diols selected from the group consisting of ethylene glycol, diethylene glycol, trimethylene glycol, 1,4-butanediol, and 1,4-cyclohexanedimethanol.

[5]

The base material for cell culture according to any of [1] to [4], wherein the dicarboxylic acid unit comprises a dicarboxylic acid unit derived from one or more dicarboxylic acids selected from the group consisting of terephthalic acid, isophthalic acid, 1,4-naphthalenedicarboxylic acid, 1,5-naphthalenedicarboxylic acid, 2,6-naphthalenedicarboxylic acid, and 2,7-naphthalenedicarboxylic acid.

[6]

The base material for cell culture according to any of [1] to [5], further comprising at least one resin selected from the group consisting of an additional polyester resin substantially free from the diol unit having the cyclic acetal structure, a polycarbonate resin, an acrylic resin, a polystyrene resin, and a polymethyl methacrylate-styrene resin.

[7]

The base material for cell culture according to [6], further comprising the additional polyester resin, wherein the additional polyester resin is at least one resin selected from the group consisting of polyethylene terephthalate, polybutylene terephthalate, isophthalic acid-modified polyethylene terephthalate, and 1,4-cyclohexanedimethanol-modified polyethylene terephthalate.

[8]
The base material for cell culture according to any of [1] to [7], wherein
the base material for cell culture is a surface-treated base material.
[9]
A container for cell culture,
comprising the base material for cell culture according to any of [1] to [8].
[10]
A cell culture method
comprising a step of culturing a cell on a base material comprising a polyester resin comprising a dicarboxylic acid unit and a diol unit, wherein
1 to 80% by mol of the diol unit is a diol unit having a cyclic acetal structure.
The cell culture method according to [10], wherein
the step of culturing the cell is a step of culturing a cell inoculated onto the base material.
[12]
The cell culture method according to [10] or [11], wherein
the base material for cell culture is a surface-treated base material.
[13]
The cell culture method according to any of [10] to [12], wherein
the cell is an adherent cell.
[14]
Use of a base material in culture of a cell, wherein
the base material comprising a polyester resin comprising a dicarboxylic acid unit and a diol unit, wherein
1 to 80% by mol of the diol unit is a diol unit having a cyclic acetal structure.

Advantageous Effects of Invention

The base material for cell culture according to the present invention allows adherent cells to proliferate at an excellent level without coating treatment.

DESCRIPTION OF EMBODIMENTS

Hereinafter, a mode for carrying out the present invention (hereinafter, simply referred to as the "present embodiment") will be described in detail. The present embodiment described below is given for illustrating the present invention and is not intended to limit the present invention thereto. The present invention can be carried out by appropriately making changes or modification without departing from the spirit of the present invention.
<Base Material for Cell Culture>
The base material for cell culture (hereinafter, also simply referred to as the "base material") of the present embodiment comprises a polyester resin comprising dicarboxylic acid units and diol units. In the polyester resin (hereinafter, also referred to as the "polyester resin of the present embodiment"), 1 to 80% by mol of the diol units is a diol unit having a cyclic acetal structure.

The base material for cell culture of the present embodiment allows cells to proliferate at an excellent level. This is presumably because, but is not limited to, the base material for cell culture of the present embodiment allows adherent cells to proliferate at an excellent level due to a polyester resin comprising 1 to 80% by mol of the diol units having the cyclic acetal structure. This presumably indicates that the structural moiety of the diol unit having the cyclic acetal structure has excellent affinity for adherent cells, and that this affinity improves adhesiveness to cells and contributes to the proliferation properties of the cells.

Furthermore, the base material for cell culture of the present embodiment is free from a coating containing an animal-derived component, and is therefore safe. In addition, the base material has undergone no coating treatment and is therefore easy to manage.

The diol units having the cyclic acetal structure preferably include diol units derived from at least one diol selected from a diol represented by the following general formula (1) and a diol represented by the following general formula (2) (hereinafter, these diols are also referred to as "compounds") in view of container formation such as the strength, transparency, and workability of the resin:

In the general formulas (1) and (2), R', $R^2$, and $R^3$ each independently represent a hydrocarbon group selected from the group consisting of an aliphatic hydrocarbon group having 1 to 10 carbon atoms, an alicyclic hydrocarbon group having 3 to 10 carbon atoms, and an aromatic hydrocarbon group having 6 to 10 carbon atoms.

The compounds represented by the general formulas (1) and (2) may be used singly or in combinations as the diol from which the diol unit having the cyclic acetal structure is derived.

The compounds represented by the general formulas (1) and (2) are preferably 3,9-bis(1,1-dimethyl-2-hydroxylethyl)-2,4,8,10-tetraoxaspiro[5.5]undecane (hereinafter, also referred to as "spiro glycol") and 5-methylol-5-ethyl-2-(1,1-dimethyl-2-hydroxyethyl)-1,3-dioxane (hereinafter, also referred to as "dioxane glycol") in view of easy availability, moldability, etc.

In the polyester resin contained in the base material for cell culture of the present embodiment, the diol units having the cyclic acetal structure preferably accounts for 1 to 80% by mol, more preferably 5 to 60% by mol, further preferably 20 to 50% by mol, of all diol units. When the diol units having a cyclic acetal structure accounts for 1% by mol or more, the cell adhesion properties tend to be exerted more sufficiently. When the diol units having the cyclic acetal structure accounts for 80% by mol or less, the crystallinity of the polyester resin is not too high, and thus, the polyester resin tends to have excellent transparency that can prevent troubles to cell observation. In short, the polyester resin of the present embodiment preferably include diol units other than the diol units having the cyclic acetal structure (hereinafter, also referred to as an "additional diol unit(s)") in all diol units. The polyester resin of the present embodiment comprising the additional diol units tends to be excellent in characteristics, such as flexibility and moldability, as a structure.

Examples of the additional diol unit include, but are not particularly limited to, aliphatic diols such as ethylene glycol, trimethylene glycol, 2-methyl-1,3-propanediol, 1,4-butanediol, 1,5-pentanediol, 1,6-hexanediol, diethylene glycol, triethylene glycol, propylene glycol, neopentyl glycol, and dineopentyl glycol; polyether diols such as polyethylene glycol, polypropylene glycol, and polybutylene glycol; trihydric or higher polyhydric alcohols such as glycerin, trimethylolpropane, ditrimethylolpropane, pentaerythritol, and dipentaerythritol; alicyclic diols such as 1,3-cyclohexanedimethanol, 1,4-cyclohexanedimethanol, 1,2-decahydronaphthalenedimethanol, 1,3-decahydronaphthalenedimethanol, 1,4-decahydronaphthalenedimethanol, 1,5-decahydronaphthalenedimethanol, 1,6-decahydronaphthalenedimethanol, 2,7-decahydronaphthalenedimethanol, tetralindimethanol, norbornanedimethanol, tricyclodecanedimethanol, isosorbide, 2,2,4,4-tetramethyl-1,3-cyclobutanediol, and pentacyclododecanedimethanol; bisphenols such as 4,4'-(1-methylethylidene)bisphenol, methylenebisphenol (bisphenol F), 4,4'-cyclohexylidenebisphenol (bisphenol Z), and 4,4'-sulfonylbisphenol (bisphenol S); alkylene oxide adducts of the bisphenols; aromatic dihydroxy compounds such as hydroquinone, resorcin, 4,4'-dihydroxybiphenyl, 4,4'-dihydroxydiphenyl ether, and 4,4'-dihydroxydiphenylbenzophenone; and alkylene oxide adducts of the aromatic hydroxy compounds.

The polyester resin of the present embodiment preferably further comprises diol units derived from ethylene glycol, diethylene glycol, trimethylene glycol, 1,4-butanediol, or 1,4-cyclohexanedimethanol, more preferably diol units derived from ethylene glycol, in view of the mechanical performance of the base material for cell culture of the present embodiment, cost efficiency, etc. These diol units listed above can be used singly or in combinations of two or more thereof.

In the polyester resin contained in the base material for cell culture of the present embodiment, examples of the dicarboxylic acid units include, but are not particularly limited to, aromatic carboxylic acids such as terephthalic acid, isophthalic acid, phthalic acid, 2-methylterephthalic acid, naphthalenedicarboxylic acid, biphenyldicarboxylic acid, and tetralindicarboxylic acid; aliphatic dicarboxylic acids such as succinic acid, glutaric acid, adipic acid, pimelic acid, suberic acid, azelaic acid, sebacic acid, dodecanedicarboxylic acid, cyclohexanedicarboxylic acid, decalindicarboxylic acid, norbornanedicarboxylic acid, tricyclodecanedicarboxylic acid, and pentacyclododecanedicarboxylic acid; and esterified products thereof.

The polyester resin of the present embodiment preferably comprises dicarboxylic acid units derived from an aromatic dicarboxylic acid such as terephthalic acid, isophthalic acid, or naphthalenedicarboxylic acid, more preferably dicarboxylic acid units derived from terephthalic acid, isophthalic acid, 1,4-naphthalenedicarboxylic acid, 1,5-naphthalenedicarboxylic acid, 2,6-naphthalenedicarboxylic acid, or 2,7-naphthalenedicarboxylic acid, in view of the mechanical performance of the base material for cell culture of the present embodiment, cost efficiency, etc. These dicarboxylic acids listed above can be used singly or in combinations of two or more thereof.

The base material for cell culture used in the present embodiment may further comprise an additional polyester resin substantially free from the diol units having the cyclic acetal structure (hereinafter, also referred to as an "additional polyester resin") or a resin other than the polyester resin. Examples of these resins include, but are not particularly limited to, polyester resins free from the diol units having the cyclic acetal structure, such as polyethylene terephthalate, polybutylene terephthalate, isophthalic acid-modified PET, 1,4-cyclohexanedimethanol-modified PET, polypropylene terephthalate, polyethylene naphthalate, poly-tetramethylcyclobutane-1,4-cyclohexanedimethyl terephthalate, poly-1,4-cyclohexanedimethyl terephthalate, polyacrylate, and liquid-crystal polyester; polycarbonate resins; polymethyl methacrylate; polyacrylonitrile resins; polystyrene resins; polymethyl methacrylate-styrene resins; polyolefin resins such as polyethylene, polypropylene, and cyclic polyolefin; polyimide resins; and nylon resins. In this context, the phrase "substantially free from the diol units having the cyclic acetal structure" means that the proportion of the diol units having the cyclic acetal structure in all diol units is less than 1% by mol. As a matter of course, the additional polyester resin also includes a polyester resin containing no diol unit having a cyclic acetal structure.

The base material for cell culture of the present embodiment can further comprise at least one resin selected from the group consisting of an additional polyester resin, a polycarbonate resin, an acrylic resin, a polystyrene resin, and a polymethyl methacrylate-styrene resin, in view of cell adhesion.

When the base material for cell culture of the present embodiment further comprises an additional polyester resin, the additional polyester resin is preferably one or more resins selected from the group consisting of polyethylene terephthalate, polybutylene terephthalate, and isophthalic acid-modified polyethylene terephthalate, in view of transparency and compatibility.

These additional polyester resins and resins other than the polyester resin listed above can be used singly or in combinations of two or more thereof.

<Method for Producing Base Material for Cell Culture>

The method for producing the base material for cell culture of the present embodiment includes, for example, the step of polymerizing a dicarboxylic acid and a diol having a cyclic acetal structure to produce a polyester resin (polymerization step), and the step of molding the polyester resin to obtain a base material (molding step). The method for producing the base material for cell culture of the present embodiment eliminates the need of a coating step in base material production. Therefore, the base material is easily produced and managed.

The polymerization step is not particularly limited as long as a dicarboxylic acid and a diol including 1,4-cyclohexanedimethanol are polymerized. A method conventionally known in the art can be applied thereto. Examples thereof can include melt polymerization or solution polymerization methods such as a transesterification method and a direct esterification method. For example, a transesterification catalyst, an esterification catalyst, an etherification inhibitor, a polymerization catalyst for use in polymerization, various stabilizers (e.g., a heat stabilizer and a light stabilizer), and a polymerization adjuster conventionally known in the art can also be used.

Examples of the transesterification catalyst include manganese, cobalt, zinc, titanium, and calcium compounds. Examples of the esterification catalyst include manganese, cobalt, zinc, titanium, and calcium compounds. Examples of the etherification inhibitor include amine compounds.

Examples of the polymerization catalyst include germanium, antimony, tin, and titanium compounds. Examples of the heat stabilizer include various phosphorus compounds such as phosphoric acid, phosphorous acid, and phenylphosphonic acid.

In the polymerization step, various additives such as an antistatic agent, a lubricant, an antioxidant, and a mold release agent, and a molding aid may be further added. The addition method is not particularly limited, and a method involving polymerization reaction for a resin in the presence of additives, etc. so that the resin contains the additives, etc.; a method involving the addition of additives, etc. to a resin in a melted state before discharge from a polymerization apparatus in the polymerization step; a method involving dry-blending additives, etc. with pellets of a resin; a method involving melt-kneading the dry blend in an extruder or the like; or a method involving the addition of additives to a melted resin in an extruder or the like, can be adopted.

The shape of the base material for cell culture used in the present embodiment is not particularly limited as long as it is acceptable to culture, including a dish, a microplate, and a flask.

The whole base material for cell culture used in the present embodiment may be constituted uniformly or almost uniformly by the polyester resin of the present embodiment. Another resin may be mixed with the polyester resin of the present embodiment, and also, other structural parts may be made of a resin of different type, glass, a metal, or the like, as long as the polyester resin of the present embodiment can be exposed on at least a face where cells adhere and are cultured (hereinafter, also referred to as a "cell culture face").

The cell culture container of the present embodiment comprises the base material for cell culture of the present embodiment. The cell culture container may be made of the base material for cell culture of the present embodiment, or may comprise a film formed of the polyester resin of the present embodiment as a base material for cell culture which film is affixed to a culture container made of a resin of different type, glass, a metal, or the like.

Alternatively, the polyester resin of the present embodiment may be formed into a net, a sphere, a thread, or a tube as the base material for cell culture used in the present embodiment, which may be put in a container made of a resin of different type, glass, or a metal, and used.

The base material for cell culture of the present embodiment is preferably a surface-treated base material in view of proliferation at a better level. The base material can be surface-treated before inoculation of cells. The surface treatment method can be a method well known to those skilled in the art and can involve treatment with, for example, γ ray, plasma, electronic beam, ultraviolet ray, or ethylene oxide gas (EOG), or treatment using an agent such as an alcohol, hydrogen peroxide water, hypochlorous acids, a surfactant, an antibiotic, an acid, or an alkali.

Among them, the surface treatment is preferably treatment with γ ray, plasma, or ultraviolet ray, more preferably treatment with ultraviolet ray, in view of the proliferation of cells at a better level. For the surface treatment with ultraviolet ray, the intensity of the ultraviolet ray correlates with an irradiation time and therefore, their ranges cannot be generalized. When the intensity of the ultraviolet ray is, for example, 0.1 to 2.0 mW/cm$^2$, the irradiation time of the ultraviolet ray is preferably 1 to 180 minutes.

<Cell Culture Method>

The cell culture method of the present embodiment has the step of culturing cells on a base material comprising a polyester resin comprising dicarboxylic acid units and diol units (culture step). In the polyester resin, 1 to 100% by mol of the diol units is a diol unit derived from 1,4-cyclohexanedimethanol.

The culture step preferably includes culturing cells inoculated onto the base material for cell culture of the present embodiment.

In the culture step, the base material for cell culture is preferably the surface-treated base material mentioned above.

In the culture step, the cells are preferably adherent cells in view of more reliably exerting the functions and effects of the present invention.

The base material for cell culture of the present embodiment is used for a wide range of cells, particularly, adherent cells. Examples thereof include, but are not particularly limited to, animal, insect, plant, and fungal cells, yeasts, and bacteria. Examples of the origin of the animal cells include, but are not particularly limited to, mammals such as humans, monkeys, African green monkeys, mice, rats, Chinese hamsters, guinea pigs, dogs, cats, pigs, sheep, and cattle; birds such as chickens; amphibians such as frogs, newts, and salamanders; and fishes such as zebrafishes, cyprinodonts, eels, goldfishes, tilapias, and minnows.

The cells for use in culture in the base material for cell culture of the present embodiment may be fibroblasts or mesenchymal stem cells, which are short-term cultured cells obtained by culture from human or animal tissues, or may be cells of an established cell line. The short-term cultured cells are preferably mammalian fibroblasts, particularly preferably human fibroblasts, or mouse fibroblasts for use as feeder cells in the growth of ES cells or iPS cells. Examples of the cell line include, but are not particularly limited to, a HeLa cell line (human uterine cervical cancer cells), a Vero cell line (African green monkey normal kidney cells), a 3T3 cell line (mouse embryonic fibroblasts), PMEF cells (mouse embryo fibroblasts), CHO cells (Chinese hamster ovary-derived cells), and MDCK (canine kidney-derived cells). The amount of cells inoculated for the culture of the cells, the culture time, the culture temperature, the medium, and the like are not particularly limited and can follow conditions usually practiced.

The use of a base material of the present embodiment is use as a base material in the culture of cells. The base material comprises a polyester resin comprising dicarboxylic acid units and diol units. Furthermore, 1 to 80% by mol of the diol units is a diol unit having a cyclic acetal structure.

EXAMPLES

Next, the present embodiment will be described more specifically with reference to Examples and Comparative Examples. However, the present embodiment is not intended to be limited by these Examples and Comparative Examples by any means.

Raw materials used in these Examples and Comparative Examples are given below.

(1) Polyethylene terephthalate (PET): manufactured by Japan Unipet Co., Ltd., trade name: UNIPET RT553C.
(2) Spiro glycol-modified PET (polyester 1): manufactured by Mitsubishi Gas Chemical Co., Inc., trade name: ALTESTER 54500 (obtained by replacing 45% by mol of ethylene glycol, which is a diol component, in a polyethylene terephthalate resin with spiro glycol).
(3) Dioxane glycol-modified PET (polyester 2): produced in the same manner as for polyester D described in Examples of Japanese Patent Laid-Open No. 2014-205773 (obtained by replacing 30% by mol of ethylene glycol, which is a diol component, in a polyethylene terephthalate resin with dioxane glycol).
(4) NDCA- and spiro glycol-modified PET (polyester 3): produced in the same manner as for polyester D described in Examples of Japanese Patent Laid-Open No. 2014-205773 (obtained by replacing 30% by mol of ethylene glycol, which is a diol component, with spiro glycol and replacing 50% by mol of terephthalic acid, which is a dicarboxylic acid component, with 2,6-naphthalenedicarboxylic acid in a polyethylene terephthalate resin).
(5) Polystyrene dish (untreated dish (without surface treatment)): manufactured by AGC TECHNO GLASS Co., Ltd., IWAKI brand, diameter: 60 mm, product code: 1010-060.
(6) Polystyrene dish (dish for tissue culture (surface-treated for adherent cells)): manufactured by AGC TECHNO GLASS Co., Ltd., IWAKI brand, diameter: 60 mm, product code: 3010-060.
(7) Polystyrene dish (collagen type 1-coated (pig-derived)): manufactured by AGC TECHNO GLASS Co., Ltd., IWAKI brand, diameter: 60 mm, product code: 4010-010.

Reference Example 1 (Method for Preparing Base Material for Cell Culture)

From PET, polyester 1, polyester 2, or polyester 3, a disk-shaped injection molding having a diameter of 50 mm and a height of 3 mm was obtained using an injection molding machine manufactured by Sumitomo Heavy Industries, Ltd. (model: SE130DU). These injection moldings of PET, polyester 1, polyester 2, and polyester 3 were each placed in the polystyrene dish (5) (untreated dish (without surface treatment) and used. The underside of each injection molding was coated with a small amount of sterilized Vaseline and attached to the bottom of the dish. The dishes (5), (6), and (7) were used as they were as to polystyrene, polystyrene surface-treated for adherent cells, and collagen-coated polystyrene, respectively.

Reference Example 2 (Cell Culture Method)

Cells were inoculated at a density of 3,000 cells/cm$^2$ onto each base material for cell culture prepared in Reference Example 1, and cultured at 37° C. for 3 days in a 5% $CO_2$ atmosphere by using, as a medium, a DMEM medium (manufactured by Gibco/Thermo Fisher Scientific Inc.) supplemented with 10% FBS and antibiotics (100 µg/mL kanamycin, 50 units/mL penicillin, and 50 µg/mL streptomycin).

Reference Example 3 (Method for Evaluating Cell Growth State)

The growth of cells was evaluated by the alamarBlue test. The culture solution was removed from each dish used in the culture in Reference Example 2, and the dish was washed with DPBS(+). Then, 4.5 mL of a DMEM medium and 0.5 mL of an alamarBlue solution (manufactured by Life Technologies Corp.) were added thereto. The dish was left standing for a predetermined time at 37° C. in a 5% $CO_2$ atmosphere under dark conditions, followed by the measurement of the absorbance of the medium. The monitor wavelength was set to 573 nm, and the reference wavelength was set to 605 nm. A value determined by subtracting the absorbance at the reference wavelength from the absorbance at the monitor wavelength was defined as a developed color value and used in the evaluation of a cell growth state. In order to eliminate the influence of the type, growth status, and passage number of the cells on the evaluation, the evaluation was conducted on the basis of a relative value to a value (100%) in the polystyrene dish (6) (dish for tissue culture (surface-treated for adherent cells)) described in Comparative Example 2 mentioned later.

Example 1

(Culture of Human Skin Fibroblast Using Spiro Glycol-Modified Polyester Resin)
A base material for cell culture was produced according to Reference Example 1 using the Spiro glycol-modified PET (2) (polyester 1) as a raw material for the base material for cell culture. Human fibroblasts were used as cells and cultured according to Reference Example 2. The cell growth state was evaluated according to Reference Example 3. The results compared with the results obtained using the polystyrene dish for tissue culture at the same time therewith are shown in Table 1.

Example 2

(Culture of PMEF Cell Using Spiro Glycol-Modified Polyester Resin)
The test was conducted in the same way as in Example 1 except that mouse embryonic fibroblasts (manufactured by Merck Millipore, PMEF cells) were used as cells. The results are shown in Table 1.

Example 3

(Culture of PMEF Cell Using Dioxane-Modified Polyester Resin)
The test was conducted in the same way as in Example 2 except that the dioxane glycol-modified PET (3) (polyester 2) was used as a raw material for the base material for cell culture. The results are shown in Table 1.

Example 4

(Culture of Human Skin Fibroblast Using NDCA- and Spiro Glycol-Modified Polyester Resin)
The test was conducted in the same way as in Example 1 except that the NDCA- and spiro glycol-modified PET (4) (polyester 3) was used as a raw material for the base material for cell culture. The results are shown in Table 1.

Example 5

Figure 1:
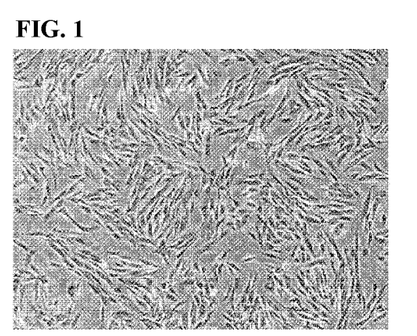
FIG. 1 is a photograph taken when a cell growth state was evaluated in Example 5.

(Culture of Human Skin Fibroblast Using Spiro Glycol-Modified Polyester Resin Irradiated with Ultraviolet Ray)
The test was conducted in the same way as in Example 1 except that the base material for cell culture before cell inoculation was irradiated with 1.8 mW/cm$^2$ of ultraviolet ray for 20 minutes. The results are shown in Table 1. FIG. 1 shows a photograph taken when the cell growth state was evaluated. The apparatus used for taking the photograph is described below. Hereinafter, the same apparatus was used for taking photographs.

Inverted phase-contrast microscope (Nikon TE200)
Photographing apparatus (Nikon DS-L1)

Example 6

(Culture of Human Skin Fibroblast Using NDCA- and Spiro Glycol-Modified Polyester Resin Irradiated with Ultraviolet Ray)

Figure 2:
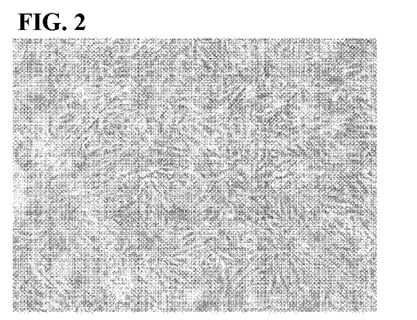
FIG. 2 is a photograph taken when a cell growth state was evaluated in Example 6.

The test was conducted in the same way as in Example 4 except that the base material for cell culture before cell inoculation was irradiated with 1.8 mW/cm$^2$ of ultraviolet ray for 20 minutes. The results are shown in Table 1. FIG. 2 shows a photograph taken when the cell growth state was evaluated.

Example 7

(Culture of Human Skin Fibroblast Using Spiro Glycol-Modified Polyester Resin Treated with Plasma)

The test was conducted in the same way as in Example 1 except that the base material for cell culture before cell inoculation was subjected to oxygen plasma treatment (100 W, 30 sec). The results are shown in Table 1.

Example 8

(Culture of human skin fibroblast using spiro glycol-modified polyester resin treated with plasma and irradiated with γ ray)

The test was conducted in the same way as in Example 1 except that the base material for cell culture before cell inoculation was subjected to oxygen plasma treatment (100 W, 30 sec) and irradiated with 25 kGy of γ ray. The results are shown in Table 1.

Example 9

(Culture of Human Skin Fibroblast Using NDCA- and Spiro Glycol-Modified Polyester Resin Treated with Plasma)

The test was conducted in the same way as in Example 4 except that the base material for cell culture before cell inoculation was subjected to oxygen plasma treatment (100 W, 30 sec). The results are shown in Table 1.

Example 10

(Culture of Human Skin Fibroblast Using NDCA- and Spiro Glycol-Modified Polyester Resin Treated with Plasma and Irradiated with γ Ray)

The test was conducted in the same way as in Example 4 except that the base material for cell culture before cell inoculation was subjected to oxygen plasma treatment (100 W, 30 sec) and irradiated with 25 kGy of 7 ray. The results are shown in Table 1.

TABLE 1

| | Example 1 | Example 2 | Example 3 | Example 4 | Example 5 | Example 6 | Example 7 | Example 8 | Example 9 | Example 10 |
|---|---|---|---|---|---|---|---|---|---|---|
| Base material for cell culture | Polyester 1 | Polyester 1 | Polyester 2 | Polyester 3 | Polyester 1 | Polyester 3 | Polyester 1 | Polyester 1 | Polyester 3 | Polyester 3 |
| Cell | Human fibroblast | PMEF cell | PMEF cell | Human fibroblast | Human fibroblast | Human fibroblast | Human fibroblast | Human fibroblast | Human fibroblast | Human fibroblast |
| UV | Not irradiated | Not irradiated | Not irradiated | Not irradiated | Irradiated | Irradiated | Not irradiated | Not irradiated | Not irradiated | Not irradiated |
| Plasma | Not irradiated | Not irradiated | Not irradiated | Not irradiated | Not irradiated | Not irradiated | Irradiated | Irradiated | Irradiated | Irradiated |
| γ ray | Not irradiated | Not irradiated | Not irradiated | Not irradiated | Not irradiated | Not irradiated | Not irradiated | Irradiated | Not irradiated | Irradiated |
| Cell growth state (vs. Comparative Example 2) | 132% | 144% | 167% | 111% | 132% | 122% | 169% | 162% | 156% | 152% |

Comparative Example 1

(Culture of Human Skin Fibroblast Using Untreated Polystyrene Resin)

Figure 3:
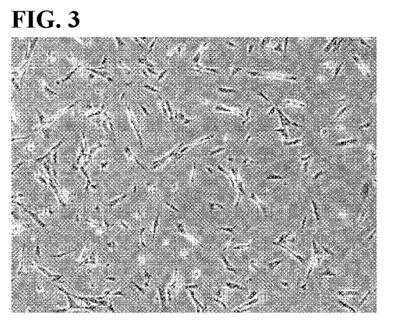
FIG. 3 is a photograph taken when a cell growth state was evaluated in Comparative Example 1.

The test was conducted in the same way as in Example 1 except that the polystyrene dish (5) (untreated dish (without surface treatment)) was used as the base material for cell culture. The results are shown in Table 2. FIG. 3 shows a photograph taken when the cell growth state was evaluated.

Comparative Example 2

(Culture of Human Skin Fibroblast Using Polystyrene Resin for Tissue Culture)

Figure 4:
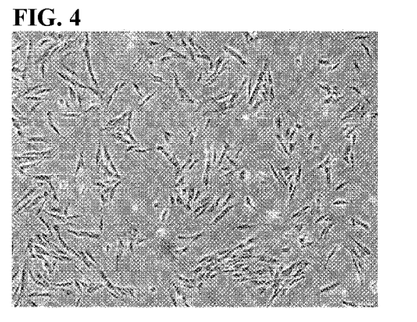
FIG. 4 is a photograph taken when a cell growth state was evaluated in Comparative Example 2.

The test was conducted in the same way as in Example 1 except that the polystyrene dish (6) (dish for tissue culture (surface-treated for adherent cells)) was used as the base material for cell culture. The results are shown in Table 2. FIG. 4 shows a photograph taken when the cell growth state was evaluated.

Comparative Example 3

(Culture of Human Skin Fibroblast Using Collagen-Coated Polystyrene Resin)

Figure 5:
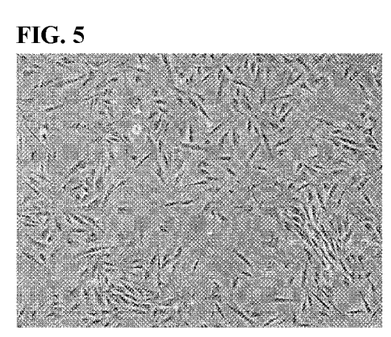
FIG. 5 is a photograph taken when a cell growth state was evaluated in Comparative Example 3.

The test was conducted in the same way as in Example 1 except that the polystyrene dish (7) (collagen type 1-coated (pig-derived)) was used as the base material for cell culture. The results are shown in Table 2. FIG. 5 shows a photograph taken when the cell growth state was evaluated.

Comparative Example 4

(Culture of Human Skin Fibroblast Using PET Resin)

The test was conducted in the same way as in Example 1 except that the polyethylene terephthalate (PET) (1) was used as the base material for cell culture. The results are shown in Table 2.

Comparative Example 5

(Culture of Human Skin Fibroblast Using PET Resin Irradiated with Ultraviolet Ray)

The test was conducted in the same way as in Example 5 except that the polyethylene terephthalate (PET) (1) was used as the base material for cell culture. The results are shown in Table 2.

culture of Comparative Example 3 coated with collagen which is an animal-derived component.

The present application is based on Japanese Patent Application No. 2015-187846 filed in the Japan Patent Office on Sep. 25, 2015, the contents of which are incorporated herein by reference.

INDUSTRIAL APPLICABILITY

The base material for cell culture according to the present invention allows adherent cells to proliferate at an excellent level without coating treatment.

Furthermore, the base material for cell culture of the present embodiment is free from a coating containing an animal-derived component, and is therefore safe. In addition, the base material has undergone no coating treatment and is therefore easy to manage. Hence, the present invention is of great industrial significance.

The invention claimed is:

1. A cell culture method comprising:
   culturing a cell on a base material comprising a polyester resin comprising a dicarboxylic acid unit and a diol unit, wherein 1 to 80% by mol of the diol unit is a diol unit having a cyclic acetal structure, wherein the base material for cell culture is a surface-treated base material that does not comprise a polystyrene support, wherein the base material is surface-treated with γ-ray, plasma, or ultraviolet ray, and wherein the cell is a fibroblast or a mesenchymal cell.

2. The cell culture method according to claim 1, wherein culturing the cell comprises culturing a cell inoculated onto the base material.

3. The cell culture method according to claim 1, wherein the polyester resin is exposed on at least a face where cell cultures adhere and are cultured.

4. A cell culture method, comprising:
   culturing a cell on a base material comprising a polyester resin comprising a dicarboxylic acid unit and a diol unit, wherein 1 to 80% by mol of the diol unit is a diol unit having a cyclic acetal structure, wherein the base material for cell culture is a surface-treated base material that does not comprise a polystyrene support, wherein the base material is surface-treated with γ-ray, plasma, or ultraviolet ray, and wherein the cell is an adherent cell.

TABLE 2

|  | Comparative Example 1 | Comparative Example 2 | Comparative Example 3 | Comparative Example 4 | Comparative Example 5 |
| --- | --- | --- | --- | --- | --- |
| Base material for cell culture | Made of polystyrene, untreated | Made of polystyrene, for tissue culture | Made of polystyrene, collagen-coated | PET | PET |
| Cell | Human fibroblast | Human fibroblast | Human fibroblast | Human fibroblast | Human fibroblast |
| UV | Not irradiated | Not irradiated | Not irradiated | Not irradiated | Irradiated |
| Cell growth state (vs. Comparative Example 2) | 67% | 100% | 115% | 101% | 96% |

All of the base materials for cell culture of Examples 1 to 10 exhibited a favorable cell growth state as compared with at least the base material for cell culture of Comparative Example 2, and exhibited an equivalent or better cell growth state even when compared with the base material for cell 5. A method for preparing a base material for cell culture, comprising:
   forming a polyester resin onto a dish for cell culture, wherein the polyester resin comprises a dicarboxylic acid unit and a diol unit, wherein 1 to 80% by mol of the diol unit is a diol unit having a cyclic acetal structure, wherein the base material for cell culture is a surface-treated base material that does not comprise a polystyrene support, wherein the base material is surface-treated with γ-ray, plasma, or ultraviolet ray, and wherein a cell for cell culture is a fibroblast or a mesenchymal cell.

6. The method for preparing a base material according to claim 5, wherein the polyester resin is exposed on at least a face where cell cultures adhere and are cultured.

* * * * *